US00PP23867P3

(12) United States Plant Patent
Bradford

(10) Patent No.: US PP23,867 P3
(45) Date of Patent: Sep. 3, 2013

(54) PEACH TREE NAMED 'GLACIER PRINCESS'

(50) Latin Name: *Prunus persica*
Varietal Denomination: Glacier Princess

(76) Inventor: Lowell Glen Bradford, Le Grand, CA (US)

( * ) Notice: Subject to any disclaimer, the term of this patent is extended or adjusted under 35 U.S.C. 154(b) by 119 days.

(21) Appl. No.: 13/374,013

(22) Filed: Dec. 8, 2011

(65) Prior Publication Data

US 2013/0152258 P1 Jun. 13, 2013

(51) Int. Cl.
*A01H 5/00* (2006.01)

(52) U.S. Cl.
USPC ..... Plt./196

(58) Field of Classification Search
USPC ..... Plt./196
See application file for complete search history.

(56) References Cited

U.S. PATENT DOCUMENTS

PP17,281 P2 12/2006 Bradford

*Primary Examiner* — June Hwu

(57) ABSTRACT

The present invention relates to a new and distinct variety of peach tree, *Prunus persica,* broadly characterized by a small size, somewhat weak, hardy, self-fertile, productive and regular bearing tree. The variety blooms during the early to mid season and requires about 475 chilling hours. The fruit matures under the ecological conditions described in mid September, with first picking on Sep. 13, 2011. The fruit is uniformly large in size, globose in shape, freestone in type, firm and melting in texture, white in flesh color, mostly red to pink in skin color, and lightly acidic in flavor.

1 Drawing Sheet

Botanical classification: *Prunus persica.*
Variety denomination: 'GLACIER PRINCESS'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'Glacier Princess'.

The present variety was hybridized by me in 2004 as a first generation cross using an unnamed yellow flesh clingstone nectarine designated by code number '52P566' as the selected seed parent and 'Snow Duchess' (U.S. Plant Pat. No. 17,281) peach as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '52P566' (unpatented) nectarine, by producing fruit that is firm, nearly full red in skin color, and that matures in mid September, but is quite distinguished therefrom by producing fruit that is white instead of yellow in flesh color, that is freestone instead of clingstone in type, and that is a peach instead of nectarine.

The present variety is most similar to its pollen parent 'Snow Duchess' peach (U.S. Plant Pat. No. 17,281) by producing peaches that are white in flesh color, mostly red to pink in skin color, globose in shape, and freestone in type, but is distinguished therefrom by producing fruit that is larger in size and that matures about thirty days later.

The present variety is similar to 'Pearl Princess V' peach (U.S. Plant Pat. No. 19,919) by having reniform leaf glands, by requiring close to 500 chilling hours, and by producing fruit that is yellowish white in flesh color, mostly red to pink in skin color, freestone in type, firm in texture, globose in shape, and has a bitter tasting kernel. However, the present variety differs from the 'Pearl Princess V' by producing fruit that is somewhat larger in size, not quite as sweet, and by maturing about 75 days later.

The present variety is similar to 'Snow Princess' peach (U.S. Plant Pat. No. 12,570) by having reniform leaf glands and by producing fruit that is nearly white in flesh color, mostly red to pink in skin color, freestone in type, firm in texture, globose in shape, and has a bitter tasting kernel. However, the present variety differs from 'Snow Princess' by producing fruit that matures about forty days later.

SUMMARY OF VARIETY

In summary, the present variety is characterized by a small size, somewhat weak in vigor, hardy, self-fertile, productive and regular bearing tree. The variety blooms during the early to mid season and requires about 475 chilling hours. The fruit matures under the ecological conditions described in mid September, with first picking on Sep. 13, 2011. The fruit is uniformly large in size, globose in shape, freestone in type, firm and melting in texture, white in flesh color, mostly red to pink in skin color, and lightly acidic in flavor.

DRAWING

The accompanying photograph consists of four whole fruits positioned to display the characteristics of the skin color and form, one divided fruit to reveal the flesh and stone, two insets to reveal buds and blossoms, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Sep. 20, 2011, on the original tree during its seventh growing season. The blossom and flower descriptions were made the previous blooming season. All major color code designations are by reference to the Inter-Society Color Council, National Bureau of Standards. Common color names are also used occasionally.

PARENTAGE

Seed parent: '52P566' (unpatented) nectarine.

Pollen parent: 'Snow Duchess' (U.S. Plant Pat. No. 17,281) peach.

TREE

Size: Small, reaching and maintaining a height of 8' [2.44 m.] and a spread of 4' [1.22 m.] after seven growing seasons utilizing typical dormant pruning.

Vigor: Medium to weak vigor, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 475 hours.

Trunk:

- *Size.*—Slender, reaching a maximum diameter of 2¼" [57.2 mm.] after the seventh growing season.
- *Texture.*—Smooth.
- *Bark color.*—A Light brownish gray [63. l.brGy] and Moderate brown [58. m.Br] variegation with Dark grayish brown [62. d.gy.Br] crevices present.
- *Lenticels.*—Approximate Number Per Square Inch: 10. Color: Deep orange yellow [69. deep OY]. Size: ¼" [6.4 mm.] to 7⁄16" [11.1 mm.]. Shape: Eye-shaped, elongated.

Branches:

- *Size.*—Diameter of limb is 1¾" [44.5 mm.] measured 12" above the crotch, 1" [25.4 mm.] measured 12" above the first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: Deep yellowish brown [75. deep yBr].
- *Lenticels.*—Number Per Square Inch: About 70 on second year wood. Color: Light yellowish brown [76. l.yBr]. Size: 1⁄64" [0.4 mm.] to 1⁄16" [1.6 mm.] on second year wood. Shape: Eye-shaped, elongated.

Leaves:

- *Size.*—Medium to large. Average Length: 6" [152.4 mm.]. Average Width: 1¾" [44.5 mm.].
- *Arrangement.*—Alternate.
- *Thickness.*—Medium.
- *Form.*—Elliptical.
- *Apex.*—Acuminate.
- *Base.*—Acute, with an average base angle of 80 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: ½" [12.7 mm.]. Average Thickness: 3⁄32" [2.4 mm.]. Color: Brilliant yellow green [116. brill.YG].
- *Stipules.*—Number: Usually 2 per leaf, up to 6 per growing tip. Average Length: ⅜" [9.5 mm.]. Color: Light yellow green [119. l.YG] becoming Light grayish yellowish brown [79. l.gy.yBr] with maturity.
- *Glands.*—Number: 2 to 4 per leaf. Position: Alternately positioned on petiole, near intersection of petiole and base of blade. Size: Medium. Form: Reniform. Color: Brilliant yellow green [116. brill.YG] becoming Dark yellowish brown [78. d.yBr] with age.
- *Leaf buds.*—Pointed, medium in size.

Flower buds:

- *Hardiness.*—Hardy, with respect to central California winters.
- *Diameter.*—Typically ⅜" [9.5 mm.] 1 week before bloom.
- *Length.*—Typically 11⁄16" [17.5 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, typically about thirty stamens, five sepal and petal locations alternately positioned.

- *Type.*—Showy, large.
- *Average flower diameter.*—2⅛" [53.4 mm.].
- *Number of petals.*—Five, extra petal fragments are observed occasionally.
- *Petal shape.*—Circular to oval.
- *Petal margin.*—Entire, somewhat wavy.
- *Average petal diameter.*—13⁄16" [20.6 mm.].
- *Average petal length.*—⅞" [22.2 mm.].
- *Petal apex.*—Rounded.
- *Petal base.*—Rounded to somewhat truncate.

*Petal color.*—Pale pink [7. p.Pk] toward the apex, Light purplish pink [249. l.pPk] toward the base on both sides.
*Anther color.*—Moderate orange [53. m.O] over a Light yellow [86. l.Y] center at bloom onset.
*Stigma color.*—Pale yellow green [121. p.YG].
*Sepal color.*—Dark purplish red [259. d.pR] on the outer surface.
*Sepal length.*—¼" [6.4 mm.].
*Sepal width.*—3/16" [4.8 mm.].
*Sepal apex.*—Rounded to elliptical to match the sepal length and width.
*Sepal margin.*—Fairly smooth.
*Average pistil length.*—11/16" [17.5 mm.].
*Average stamen length.*—9/16" [14.3 mm.].
*Fragrance.*—Moderate.
*Blooming period.*—Early to medium, five days after 'Snow Princess' (U.S. Plant Pat. No. 12,570) peach.
*Onset of bloom.*—One percent on Feb. 20, 2011.
*Date of full bloom.*—Mar. 2, 2011.
*Duration of bloom.*—One to two weeks, dependent on ambient temperature.
*Number per cluster.*—1 to 3 with single flowers most common.

FRUIT

Maturity when described: Firm ripe, Sep. 20, 2011.
Date of first picking: Sep. 13, 2011.
Date of last picking: Sep. 27, 2011.
Size: Uniform, large.
*Average diameter axially.*—3¼" [82.6 mm.].
*Average diameter across suture plane.*—3½" [88.9 mm.].
*Average diameter across cheek plane.*—3½" [88.9 mm.]
*Typical weight.*—12.9 ounces [365.7 grams].
Form: Uniform, globose, slightly asymmetrical.
*Longitudinal section form.*—Oval to circular.
*Axial view.*—Circular with a slight suture bulge.
Suture: Extends from the base, along the side, to the pistil point.
*Near the base.*—A shallow groove.
*Along the side.*—A distinct line.
*Near the apex.*—A shallow groove.
Ventral surface: Rounded, lipped throughout.
Lips: Slightly unequal.
Cavity: Flaring, circular to slightly elongated in the suture plane, suture showing on one side, Yellowish white [92. yWhite] stem markings typical.
*Depth.*—¾" [19.1 mm.].
*Breadth.*—1 7/16" [36.5 mm.].
Base: Truncate.
Apex: Rounded, with very few mammiform.
Pistil point: Apical, very short in length, usually depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed in dry season.
*Color.*—Moderate red [15. m.R] smoothly blending into Pale yellowish pink [31. p.yPk] with some Pale yellow [89. p.Y] sun protected areas.
*Down.*—Short, does not roll up when rubbed.
Flesh:
*Color.*—Yellowish white [92. yWhite] with Moderate red [15. m.R] bleeding around the stone.
*Surface of pit cavity.*—Covered with Dark reddish orange [38. d.rO] fibers.
*Amygdalin.*—Scarce.
*Juice.*—Moderate, rich.
*Texture.*—Firm, tough. meaty.
*Fibers.*—Few, fine, tender.
*Ripens.*—Earlier toward the apex.
*Flavor.*—A tasty balance of sugar with slight acid, typically 16 brix.
*Aroma.*—Moderate.
*Eating quality.*—Good.

STONE

Type: Freestone.
Form: Oval.
Hilum: Narrow.
Base: Acute.
Apex: Rounded to flat.
Sides: Equal.
Surface: Irregularly furrowed throughout, pitted toward the base.
Ridges: Slightly jagged.
External color: Grayish reddish brown [46. gy.rBr].
Pit wall color when cracked: Light reddish brown [42. l.rBr].
Cavity surface color: Moderate olive [107. m.Ol].
Average pit wall thickness: ¼" [6.4 mm.]
Average width: 1 1/16" [27.0 m.].
Average length: 1½" [38.1 mm.].
Average breadth: ¾" [19.1 mm.].
Tendency to split: None observed.
Kernel:
*Form.*—Oval.
*Skin color.*—Strong yellowish brown [74. s.yBr] when first removed.
*Pellicle color.*—Deep yellowish brown [75. deep yBr].
*Vein color.*—Deep yellowish brown [75. deep yBr].
*Taste.*—Bitter.
*Viable.*—Yes.
*Average width.*—9/16" [14.3 mm.].
*Average length.*—13/16" [20.6 mm.].
*Amygdalin.*—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its pollen parent 'Snow Duchess' peach (U.S. Plant Pat. No. 17,281) by producing peaches that are white in flesh color, mostly red to pink in skin color, globose in shape, and freestone in type, but is distinguished therefrom by producing fruit that is larger in size and that matures about thirty days later.

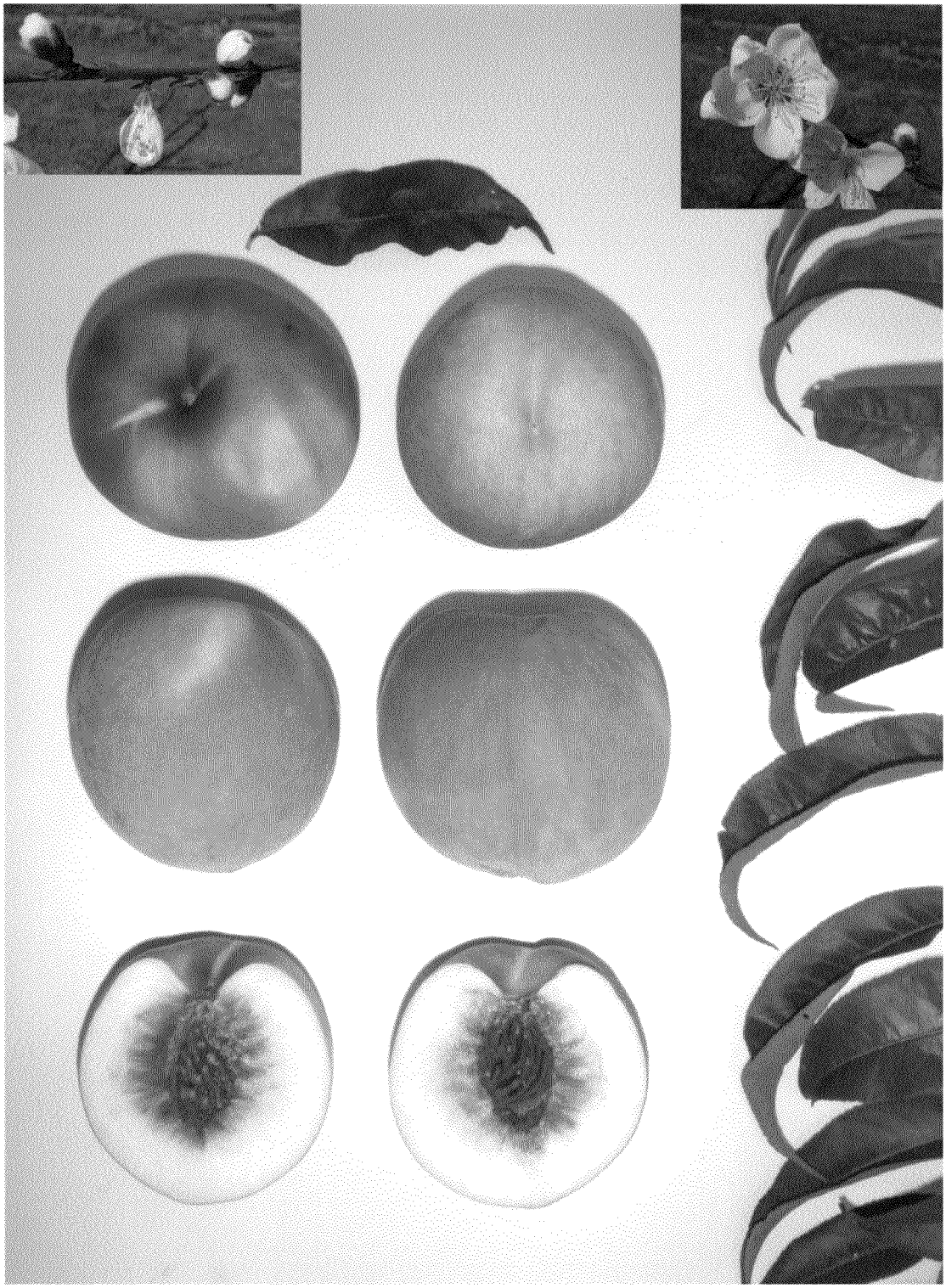

* * * * *